United States Patent [19]
Richter

[11] Patent Number: 5,336,062
[45] Date of Patent: Aug. 9, 1994

[54] MICROMINIATURIZED PUMP

[75] Inventor: Axel Richter, München, Fed. Rep. of Germany

[73] Assignee: Fraunhofer-Gesellschaft zur Forderung der angewandten Forschung e.V., München, Fed. Rep. of Germany

[21] Appl. No.: 920,584

[22] Filed: Oct. 20, 1992

[30] Foreign Application Priority Data

Feb. 27, 1990 [DE] Fed. Rep. of Germany ....... 4006152

[51] Int. Cl.$^5$ ................................. F04B 17/00
[52] U.S. Cl. .................. 417/413 A; 417/413 B
[58] Field of Search ............ 417/48, 50, 322, 413 A, 417/413 B

[56] References Cited
U.S. PATENT DOCUMENTS

| 3,963,380 | 6/1976 | Thomas et al. .............. 417/322 |
| 5,224,843 | 7/1993 | Lintel .......................... 417/413 A |

FOREIGN PATENT DOCUMENTS

| 0392978 | 4/1990 | European Pat. Off. ...... F04B 43/04 |
| 9107591 | 5/1991 | European Pat. Off. ........ 417/413 A |
| 9201160 | 1/1992 | European Pat. Off. ........ 417/413 A |
| 3802545 | 8/1989 | Fed. Rep. of Germany ... 417/413 B |
| 1542799 | 12/1977 | United Kingdom ......... F04B 43/00 |

OTHER PUBLICATIONS

Van De Pol et al., "A Piezoelectric Micropump based on Micromachining of Silicon", Sensors and Actuators, Feb. 1988, pp. 153–167.

Ohnstein et al., "Micromachined Silicon Microvalve", Apr. 1990, pp. 95–98.

Richter et al., "An Electrohydrodynamic Micropump", 3rd IEEE Workshop on Micro Electro Mechanical Systems, Feb. 1990.

Peterson, "Silicon as a Mechanical Material", Proceedings of the IEEE, vol. 70, No. 5, May 1982.

Eashi et al., "Normally Closed Microvalve and Micropump Fabricated on a Silicon Vapor", Sensors and Actuators, 20, Feb. 1989, pp. 163–169.

Primary Examiner—Louis J. Casaregola
Assistant Examiner—Alfred Basichas
Attorney, Agent, or Firm—Ralph H. Dougherty

[57] ABSTRACT

A microminiaturized pump consists of two superposed, interconnected pump bodies of semiconductor material, which each include electrically conductive regions insulated from one another. At least one of the two pump bodies has a thin, flexible diaphragm having integrated therein at least one check valve, which has an inlet aperture and a cover plate over it, the thin, flexible diaphragm including at least part of the electrically conductive region of one pump body, whereas, in relation to the surface dimensions of the thin, flexible diaphragm, the electrically conductive region of the other pump body is arranged at a short distance from the thin, flexible diaphragm.

17 Claims, 3 Drawing Sheets

MICROMINIATURIZED PUMP

DESCRIPTION

The present invention refers to a microminiaturized pump comprising at least one first and one second pump body, which are arranged one on top of the other and which are interconnected, at least one of said pump bodies consisting at least partially of a semiconductor material, and both pump bodies including electrically conductive regions, which are insulated from one another, according to the generic clause of patent claim 1.

The technical publication A. Richter and H. Sandmaier "An Electrohydrodynamic Micropump", IEEE MEMS-90, Feb. 12 to 14, 1990, Napa Valley, Calif., U.S.A., discloses such a microminiaturized pump. This micropump, which is known from the above-mentioned technical publication put in circulation on the occasion of a professional meeeting, corresponds to the micropump which is disclosed in the prior, non-prepublished application P 39 25 749.5-32 owned by the applicant. This known microminiaturized pump is an electrohydrodynamic injection pump whose pump bodies, which are spaced apart in the pumping direction, are constructed as grid-shaped semiconductor electrodes provided with surface metallization. In the case of this pump, one of the two grid-shaped electrodes injects ions into the gas to be pumped, or into the liquid to be pumped, which must necessarily be insulating. The movement of the ions relative to the gas to be pumped or to the liquid to be pumped produces a pumping effect so that this known electrostatic pump is capable of functioning without any moving parts. Said known pump, however, is neither suitable for pumping nor for dosing aqueous solutions or other conductive media.

A microminiaturized pump working according to a different operational principle is known from the technical publication F. C. M. van de Pol et al., "A Thermopneumatic Micropump based on Micro-Engineering Techniques" of the conference report "Transducers '89" The 5th International Conference on Solid-State Sensors and Actuators & Eurosensors III, Jun. 25 -30, 1989, Montreux, Switzerland. In the case of this known micropump, a heating resistor is located in a gas-filled chamber closed by a diaphragm. The gas volume can be increased and reduced by heating and by cooling the heating resistor. The diaphragm of the chamber can thus be actuated electrically. A chamber with the liquid to be pumped is located on the diaphragm side facing away from the heating resistor, said chamber being closed by a check valve on the inlet side as well as on the outlet side, and this means that a movement of the diaphragm will pump the liquid enclosed in the chamber. This known micropump is composed of five different sandwich structures, which have to be produced in separate manufacturing processes before they can be combined so as to form the micropump. Hence, this micropump requires high manufacturing expenditure. Furthermore, it has comparatively large dimensions and a power consumption in the order of approx. 2 watts, although its transport capacity —in the order of a few microliters per minute—is low.

The technical publication M. Esashi, et. al., "Normally Closed Microvalve and Micropump Fabricated on a Silicon Wafer", Sensors and Actuators, 20, 1989, pages 163 to 169, discloses a diaphragm-type micropump working according to a piezoelectric operational principle which deviates from the operational principles of the above-explained micropump. The known pump essentially comprises a piezoelectric actuating member connected via glued joints with a diaphragm structure, which is, in turn, connected with a plate-shaped valve seat glass structure. This known pump does not only require high operating voltages in the order of 100 V for controlling the piezoelectric actuating element, but—having dimensions of $20 \times 20 \times 10$ mm—it also takes up too much space for many cases of use.

The technical publication T. Ohnstein, "Micromachined Silicon Microvalve", Proceedings IEEE, Feb. 11-14, 1990, Napa Valley, Calif., U.S.A., already discloses an electrostatically actuable silicon microvalve for modulating a flow of gas in an electrically controllable manner. The known microvalve consists of a silicon base plate having an inlet opening on which a dielectric layer is arranged, said dielectric layer merging with a movable cover plate. The cover plate encloses a first electrode surface which is arranged in opposite relationship with a second electrode surface within the dielectric layer. By applying a suitable control voltage, the normally open valve can be brought to a closed state.

In comparison with this prior art, the present invention is based on the task of further developing a microminiaturized pump of the type mentioned at the beginning in such a way that it can be produced with technologies suitable for bulk series production as a pump permitting a high degree of miniaturization and having low power consumption.

In the case of a microminiaturized pump according to the generic clause of patent claim 1, this task is solved by the features disclosed in the characterizing clause of patent claim 1.

In the case of the microminiaturized pump according to the present invention, at least one of the two pump bodies has a thin, flexible, diaphragm-like region having arranged therein at least one check valve, preferably a plurality of check valves. Each check valve is formed integrally with the thin, flexible, diaphragm-like region and has an inlet aperture as well as a cover plate, which is arranged in opposed relationship with said inlet aperture and which covers said aperture, one of the narrow sides of said cover plate merging with the thin, flexible, diaphragm-like region. The thin, flexible, diaphragm-like region includes at least part of the electrically conductive region of one of the two pump bodies, whereas, in relation to the surface dimensions of the thin, flexible, diaphragm-like region, the electrically conductive region of the other pump body is arranged at a short distance from said thin, flexible, diaphragm-like region. The thus created, integrated diaphragm-valve-pump structure of the microminiaturized pump according to the present invention can be produced with manufacturing techniques in the field of semiconductor technology.

A special advantage of the microminiaturized pump according to the present invention is to be seen in the fact that, when the back of at least one of the two pump bodies is electrically insulated, said pump can be used for pumping and dosing aqueous or conductive solutions and liquids of the type occurring especially in the field of medicine and biotechnology. Hence, the pump according to the present invention is particularly important with regard to incorporal application modes for dosing arbitrary liquid medicaments, this mode of application being possible for the first time on the basis of the degree of microminiaturization of the pump which has been achieved in accordance with the present invention.

An additional important advantage of the microminiaturized pump according to the present invention is to be seen in the fact that, due to its production process, it also permits integration with sensors and electric control elements so as to form one microsystem.

Preferred further developments of the microminiturized pump according to the present invention are disclosed in the subclaims.

In the following, preferred embodiments of the present invention will be explained in detail with reference to the drawings enclosed, in which.

Figure 1:
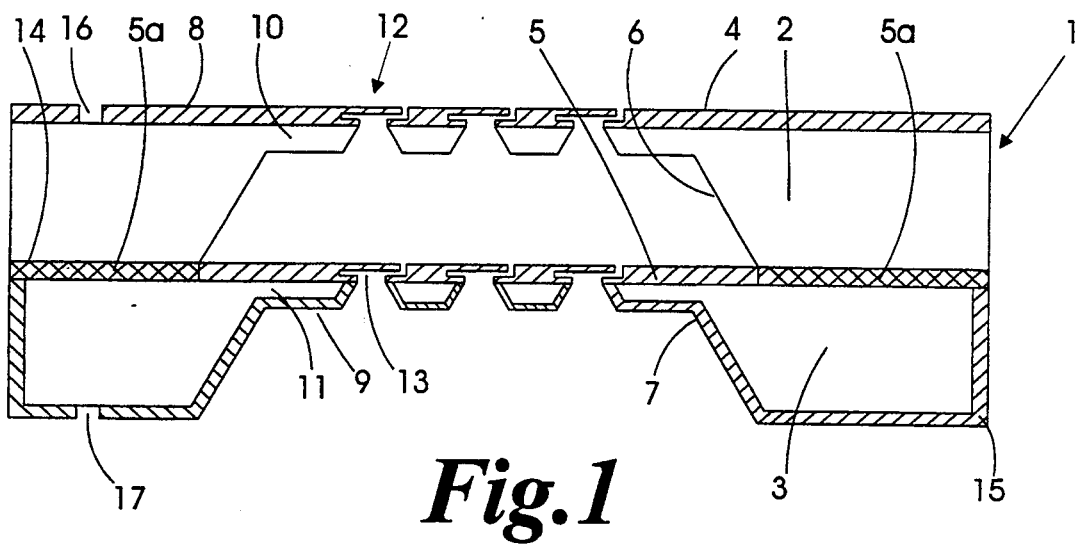
FIG. 1 shows a vertical sectional view of a first embodiment of the microminiaturized pump according to the present invention.

The embodiment of the microminiaturized pump for pumping fluids or gases according to the present invention which is shown in FIG. 1 is provided with reference numeral 1 in its entirety and comprises essentially a first pump body 2 arranged on top of a second pump body 3 and fixedly connected thereto. Both pump bodies 2, 3 consist of silicon. The front of the pump bodies 2, 3 is provided with a silicon nitride layer 4, 5 having a thickness of from approx. 1 to 5 micrometers. Each pump body 2, 3 is provided with a rear recess 6, 7, which is produced by photolithographic determination of a rear etch opening and by subsequent anisotropic etching. As is, in principle, known, such anisotropic etching in silicon can be carried out e.g. by means of an approx. 30% KOH solution. By means of the rear, frustoconical recesses 6, 7, thin, flexible, diaphragm-like regions 8, 9 are defined within the pump bodies 2, 3. In the case of the embodiment shown, said thin, flexible diaphragm-like regions consist of a silicon diaphragm 10, 11 and of the silicon nitride layer 4,5, located on top of said silicon diaphragm.

Preferably, each of the layers referred to as silicon nitride layers 4, 5 hereinbelow comprises a sequence of layers consisting of a thermal oxide layer 4a of from 100 to 300 nm thickness, a first silicon nitride sublayer 4b of from 400 to 1000 nm thickness and a second silicon nitride sublayer 4c of from 400 to 2000 nm thickness, as can especially be seen from FIG. 2.

Figure 2:
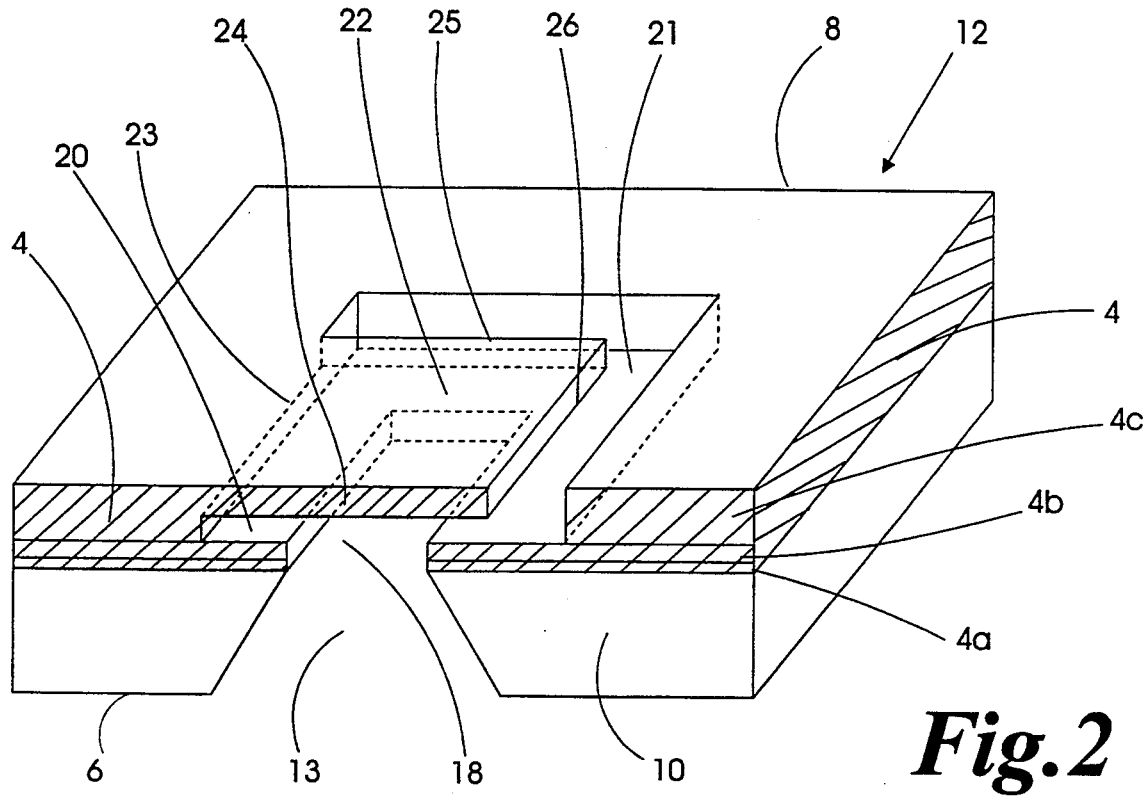
FIG. 2 shows a perspective view of a valve structure within the diaphragm, a plurality of such valve structures being included in the pump according to FIG. 1.

A plurality of check valves 12, 13, which are arranged in a fieldlike array and the structure of which will be explained in detail hereinbelow with reference to FIG. 2, is arranged within each thin, flexible, diaphragm-like region 8, 9.

The back of the first pump body 2 is connected to a front oxide layer 5a of the second pump body 3 by means of an intermediate Pyrex layer 14 with the aid of electrostatic bonding.

The pump bodies 2, 3 can also be glued together. For the purpose of electric insulation, the second pump body 3 is provided with a thermal oxide layer 15 towards its back. This thermal oxide layer 15 defines together with the silicon nitride layer 5 of the second pump body 3 an electric insulation encompassing said second pump body 3 completely. The two potentials of an a.c. voltage are applied to the first pump body 2 via a first ohmic contact 16 and to the second pump body 3 via a second ohmic contact 17. Due to the electrostatic forces generated by the a.c. voltage applied, the thin, flexible, diaphragm-like regions 8, 9 of the pump 1 are caused to vibrate in opposite phase to one another. Preferably, the frequency of the a.c. voltage applied is chosen such that it corresponds to the first basic mechanical vibration of the two diaphragm-like regions 8, 9. The diaphragm lift and, consequently, the pumping quantity of the pump 1 can be adjusted exactly by choosing an adequate frequency and an adequate voltage value.

FIG. 2 shows a perspective view of a check valve 12 provided in the case of pump 1 according to FIG. 1. As can be seen in detail in FIG. 2, the check valve 12 lies within the thin, flexible, diaphragm-like region 8 comprising the silicon nitride layer 4 and the silicon diaphragm 10. The valve 12 has an inlet aperture 18, which is arranged in the lowermost plane of the silicon nitride layer 4 and which has a cross-section of e.g. 25×60 micrometers. The inlet aperture 18 communicates via a rear recess 19, which is produced by anisotropic etching, with the rear recess 6 of the first pump body 2.

In a central plane of the silicon nitride layer 4, a planar recess 20 is positioned, which is arranged centrically with the inlet aperture 18. A boundary recess 21, which, when seen in a top view of the thin, flexible, diaphragm-like region 8, is essentially U-shaped, extends in the vertical direction downwards down to the planar recess 20, whereby a cover plate 22 is defined, which merges integrally with the silicon nitride layer 4 on one of its narrow sides 23, whereas the other narrow sides 24, 25, 26 are bordered by the boundary recess 21. The cover plate 22 is thus positioned centrically above the inlet aperture 18 and is spaced apart a short distance of e.g. 1 micrometer therefrom. Due to the intrinsic elasticity of the cover plate 22, said cover plate 22 defines together with the inlet aperture 18 a check valve 12, since, in the case of a fluid pressure acting from the back, the cover plate 22 can be bent away from the inlet aperture 18 due to its intrinsic elasticity and, consequently, said inlet aperture 18 will be opened, whereas in the case of a fluid pressure acting from the front of the nitride layer 4, the cover plate 22 will contact the inlet aperture 18 from above, whereby said inlet aperture will be closed.

For producing the pump 1 according to the present invention, which is shown in FIG. 1 and 2, the first nitride layer 4b is first applied to the oxide layer 4a of the thermally oxidized silicon wafer, a window-shaped recess for determining the inlet aperture 18 being then etched into said first nitride layer 4b in a photolithographic etching process. By means of an adequate mask, a sacrificial layer is introduced in the inlet aperture 18 and in the region of the future planar recess 20, said sacrificial layer having a thickness of from 400 to 2000 nm, preferably 1000 nm, and consisting e.g. of PBSG or of a metal. This structure is covered by the second nitride layer 4c, which is outlined in FIG. 2. In an additional photolithographic step, the boundary recess 21 is defined and etched. In an additional etching step, the sacrificial layer is removed by means of a selective etching process, the nitride layer being not attacked by said etching process. Following this, the rear recess 6 and, subsequently, the rear recesses 19 are determined and etched free by two successive photolithographic and etching steps. If an insulation of the semiconductor pump body is desired, such insulation can now be provided by means of thermal oxidation of the silicon. Other possibilities of providing an insulation are the application of an insulating material by means of chemical vapour deposition or by means of sputtering.

Deviating from the method described hereinbefore, the method step of selectively etching the sacrificial layer can also be carried out after the etching of the rear recess 19 and of the inlet aperture 18.

By applying an intermediate Pyrex layer 14, the back of the first pump body 2 is connected to the front silicon nitride layer 5 of the second pump body 3 by means of electrostatic bonding.

For operating the electrostatic pump according to the invention, which has the structure shown in FIG. 1, with a low a.c. voltage, it is necessary that the mutual distance of the two diaphragm-like regions 8, 9 is much smaller than the lateral dimensions of said diaphragm-like region 8, 9. Normally, silicon wafers have a thickness of approx. 500 micrometers. However, in order to be able to operate the embodiment of the pump 1 according to the invention, which is shown in FIG. 1, with a low voltage, it will be necessary to reduce at least the thickness of the first pump body 2 to a thickness of preferably 5 to 20 micrometers.

In the following, second to fifth embodiments of the pump according to the present invention will be explained in detail with reference to FIGS. 3 to 6. With the exception of the deviations explained hereinbelow, these embodiments correspond to the embodiment according to FIGS. 1 and 2 so that a renewed explanation of identical or similar parts or production methods can be dispensed with.

Figure 3:
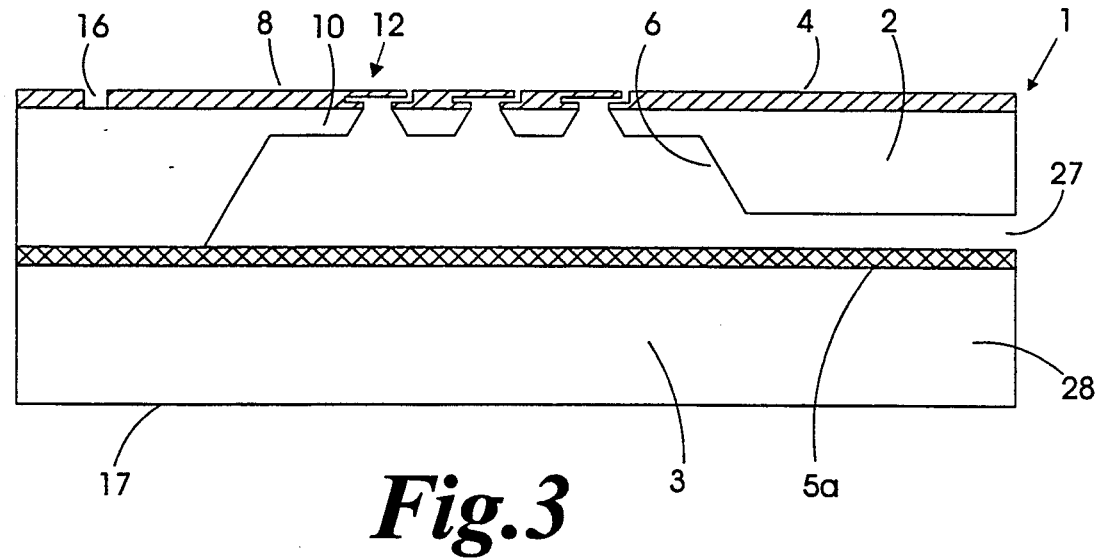
FIGS. 3 to 6 show vertical sectional views of second to fifth embodiments of the microminiaturized pump according to the present invention.

In the case of the second embodiment of the pump according to the present invention, which is shown in FIG. 3, the first pump body 2 identically corresponds to the first pump body 2 of the first embodiment according to FIG. 1 and FIG. 2, respectively, with the exception of a lateral passage arranged on the lower surface thereof.

The second pump body 3, however, is here a flat silicon body 28, which has an oxide-Pyrex layer 5a provided thereon and which only fulfils the function of a counterelectrode for the diaphragm-like region 8 of the first pump body 2. To the person skilled in the art, it will be self-evident that, for achieving a pumping effect, a second set of check valves can be dispensed with at least in cases in which the pump is used for conveying a liquid, which, due to its inertia, is maintained in a continuously flowing condition, when the thin, flexible, diaphragm-like region 8 of the first pump body 2 carries out oscillating vibrations.

Figure 4:
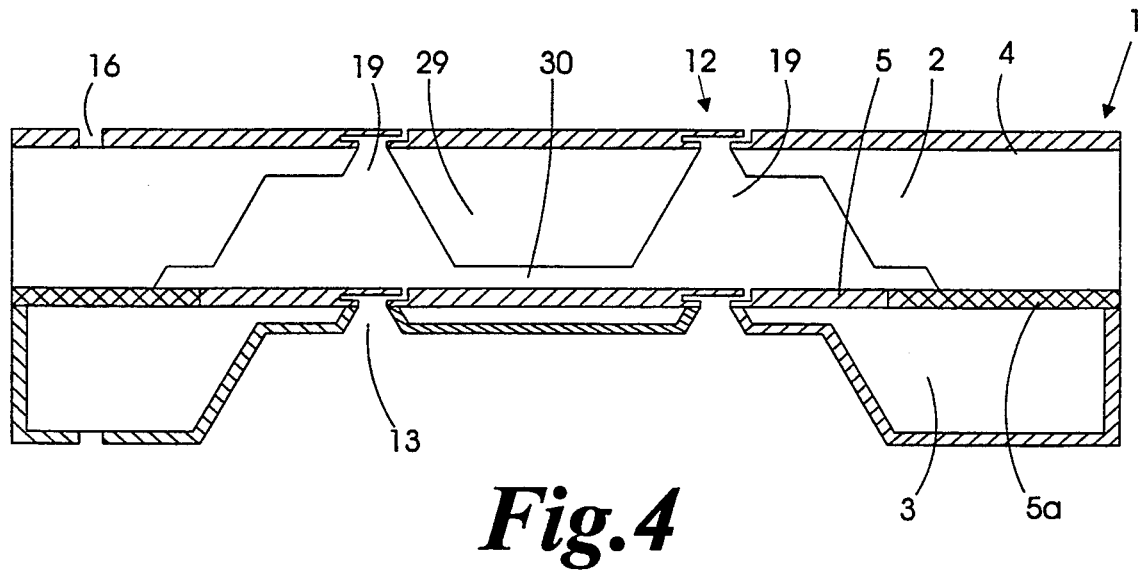

In the case of third embodiment according to FIG. 4, however, the second pump body 3 essentially corresponds to the second pump body 3 of the first embodiment according to FIG. 1. However, in the case of said third embodiment of the pump 1 according to the present invention, which is shown in FIG. 4, the thin, flexible, diaphragm-like region 8 of the first pump body 2 has been replaced by a rigid counterelectrode region 29, which is defined due to the fact that, in the case of the embodiment shown in said FIG. 4, the rear recess 30 is etched into the first pump body 2 by means of an anisotropic etching process such that its depth seen relative to the back of the silicon wafer of said first pump body 2 only corresponds to the desired electrode spacing of from 5 to 20 micrometers. It is thus possible to maintain the original thickness of the silicon wafer 2 of approx. 500 micrometers, since, in the case of this embodiment, the thickness of the silicon wafer is independent of the magnitude of the electrode spacing.

Figure 5:
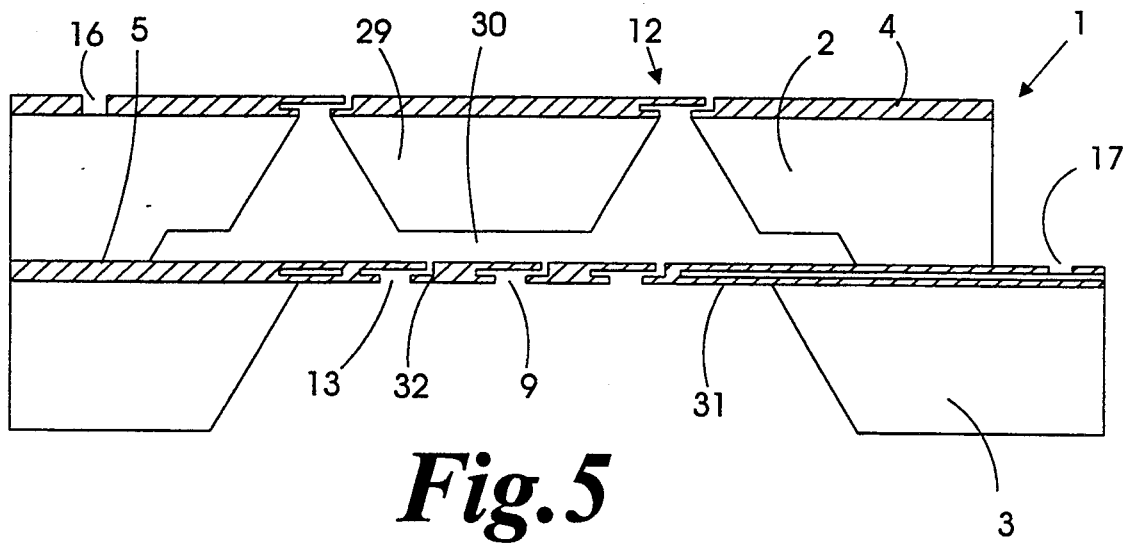

The embodiment according to FIG. 5, which represents the fourth embodiment of the pump 1 according to the present invention, corresponds identically to the third embodiment according to FIG. 4 as far as the first pump body is concerned. The second pump body 3 consists in its thin, flexible, diaphragm-like region 9 exclusively of the silicon nitride layer 5, which has embedded therein a metal electrode layer 31 in such a way that said metal electrode layer is enclosed by the silicon nitride layer 5 on all sides. The metal electrode layer within said silicon nitride layer 5 has electrode openings 32 in the area of the check valves 13 so that the movement of the cover plates 22 is independent of the control voltage applied.

Figure 6:
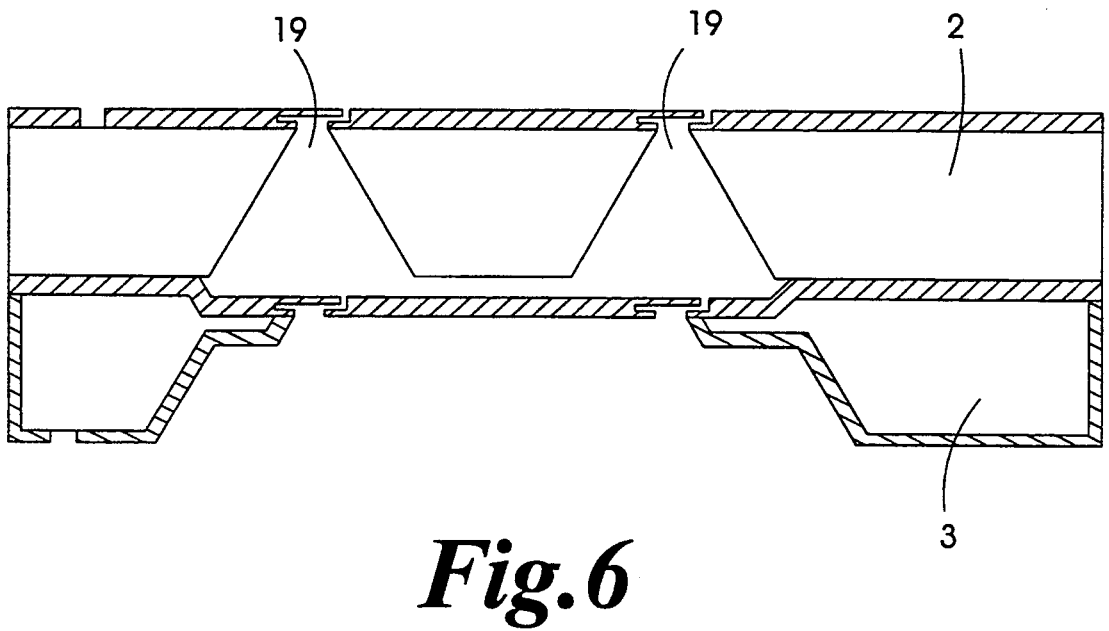

The fifth embodiment of the pump 1 according to the present invention differs from the fourth embodiment according to FIG. 5 with regard to the fact that the back of the first pump body 2, which faces the second pump body 3, is essentially flat leaving out of account the rear recesses 19. Instead of the rear spacing recess 30 of the first pump body 2 in the case of the third embodiment according to FIG. 4, the second pump body 3 is here provided with a front spacing recess 33, which is produced by anisotropic etching and by means of which the thin, flexible, diaphragm-like region 9 of the second pump body is displaced by the desired electrode spacing towards the back of said second pump body. Just as in the case of the embodiment according to FIG. 4, the fifth embodiment according to FIG. 6 provides the advantage that the wafer thickness is independent of the desired electrode spacing.

Deviating from the pump structures shown in FIGS. 1 to 6, more than two pump bodies may be arranged one on top of the other in the case of high pumping pressures or in cases in which it may perhaps be considered necessary to reduce the pressure applied to the valves.

Instead of silicon which is preferably used as a starting material for all pump bodies, it is also possible to produce only one pump body from silicon or from some other semiconductor material and to produce the other pump body from some other suitable material. Especially in the case of the embodiment according to FIG. 3, any material which is adapted to be used as an electrode can be used for the second pump body 3.

In the case of the embodiments shown, only the conductive semiconductor region of one 3 of the two pump bodies 2, 3 was electrically insulated from the fluid to be pumped by means of a fully encompassing insulating layer 5, 15. If complete potential isolation is desired, it will, of course, be possible to insulate also the second pump body in a corresponding manner.

I claim:

1. An electrostatically actuatable microminiaturized pump comprising:
    at least one first and one second pump body which are arranged one on top of the other and which are interconnected, at least one of said pump bodies comprising at least partially of a semiconductor material, and both pump bodies having electrically conductive regions, which are electrically insulated from one another;
    at least one of said two pump bodies has a thin, flexible diaphragm;
    at least one check valve is arranged within said thin, flexible diaphragm, said check valve being formed integrally with said thin, flexible diaphragm and having an inlet aperture as well as a cover plate, which covers said inlet aperture and which merges with said thin, flexible diaphragm at one of its narrow sides;

said thin, flexible diaphragm includes at least part of said electrically conductive region of said pump body; and in relation to the surface dimensions of said thin, flexible diaphragm, said electrically conductive region of said other pump body being arranged at a short distance from said thin, flexible diaphragm.

2. An electrostatically actuatable microminiaturized pump according to claim 1, wherein said electrically conductive region of at least one of said pump bodies is enclosed by an electrically insulating layer on all sides.

3. An electrostatically actuatable microminiaturized pump according to claim 1, wherein said first pump body, which includes said thin, flexible diaphragm and which partially consists of a semiconductor material, is provided with a front dielectric layer, in which said check valve is formed, and with a rear recess produced by anisotropic etching and defining said thin, flexible diaphragm.

4. An electrostatically actuatable microminiaturized pump according to claim 3, wherein said dielectric layer is a layer of silicon nitride or a layer of thermal oxide and silicon nitride.

5. An electrostatically actuatable microminiaturized pump according to claim 3, wherein said inlet aperture of said check valve is positioned in a plane of said dielectric layer which extends in spaced relationship with the front side of said thin, flexible diaphragm, and said inlet aperture communicates with said rear recess via a second rear recess produced by anisotropic etching.

6. An electrostatically actuatable microminiaturized pump according to claim 5, wherein a planar recess is provided between said cover plate and said inlet aperture, said cover plate being spaced from said inlet aperture by means of said planar recess, and a boundary recess, which, when seen in a top view of said thin, flexible diaphragm, is essentially U-shaped and extends down to said planar recess defining the narrow sides of said cover plate, said cover plate does not merge with said thin, flexible diaphragm.

7. An electrostatically actuatable microminiaturized pump according to claim 3, wherein said electrically insulating layer enclosing said electrically conductive region on all sides is formed, on the one hand, by said front dielectric layer and, on the other hand, by a rear insulating layer.

8. An electrostatically actuatable microminiaturized pump according to claim 7, wherein said rear insulating layer is formed by a thermal oxide of said semiconductor material of said pump body.

9. An electrostatically actuatable microminiaturized pump according to claim 7, wherein said rear insulating layer is formed by an insulator, which is chemically applied to the back of said pump body in a vapor deposition process.

10. An electrostatically actuatable microminiaturized pump according to claim 7, wherein said rear insulating layer is formed by an insulating material applied to the back of said pump body by means of sputtering.

11. A microminiaturized pump according to claim 3, characterized in that the first pump body (2) is additionally provided with a front spacing recess (33), which is produced by anisotropic etching and which defines the thin, flexible, diaphragm-like region (9) together with the rear access (6), and that the front dielectric layer (5) is arranged in said front spacing recess (33).

12. A microminiaturized pump according to claim 11, characterized in that, at its back facing the pump body (3), the other pump body (2) is essentially flat, and that the front recess (33) of said first-mentioned pump body (3) determines a spacing between the thin, flexible, diaphragm-like region (9) and the back of said other pump body (2).

13. A microminiaturized pump according to claim 3, characterized in that the conductive region of one pump body (2, 3) is formed by a metal electrode layer (31) embedded in the dielectric layer (5) and provided with electrode openings (32) in the area of the valves (12, 13).

14. An electrostatically actuatable microminiaturized pump according to claim 1, wherein both pump bodies consist essentially of silicon.

15. An electrostatically actuatable microminiaturized pump according to claim 1, wherein said two pump bodies are interconnected via an intermediate Pyrex layer by means of electrostatic bonding.

16. A microminiaturized pump according to claim 3, characterized in that one of the pump bodies is provided with a thin, flexible, diaphragm-like region (9), and that the conductive region of the other pump body (2) extends up to a point located close to said thin, flexible, diaphragm-like region (9) of said first-mentioned pump body (3).

17. A microminiaturized pump according to claim 16, characterized in that the dielectric layer (5) of one pump body extends as a plane over the surface thereof, and that the other pump body (2) is provided with a spacing recess (30), which is produced by anisotropic etching and which is located at the pump body back facing the pump body (3).

* * * * *